(12) United States Patent
Meier et al.

(10) Patent No.: US 8,578,780 B2
(45) Date of Patent: Nov. 12, 2013

(54) APPARATUS FOR INTERNAL INSPECTION OF A WORKPIECE HAVING A HOLLOW CYLINDRICAL HOLE

(71) Applicant: intelligeNDT Systems & Services Gmbh, Erlangen (DE)

(72) Inventors: Rainer Meier, Erlangen (DE); Edgar Zaus, Nürnberg (DE)

(73) Assignee: Intelligendt Systems & Services GmbH, Erlangen (DE)

( * ) Notice: Subject to any disclaimer, the term of this patent is extended or adjusted under 35 U.S.C. 154(b) by 0 days.

(21) Appl. No.: 13/786,522

(22) Filed: Mar. 6, 2013

(65) Prior Publication Data

US 2013/0180338 A1    Jul. 18, 2013

Related U.S. Application Data

(63) Continuation of application No. PCT/EP2011/065212, filed on Sep. 2, 2011.

(30) Foreign Application Priority Data

Sep. 6, 2010   (DE) .......................... 10 2010 040 274

(51) Int. Cl.
*G01N 29/22*         (2006.01)
(52) U.S. Cl.
USPC .......................................................... 73/632
(58) Field of Classification Search
USPC .................... 73/632, 623, 624, 628
See application file for complete search history.

(56) References Cited

U.S. PATENT DOCUMENTS

| 4,576,048 A | * | 3/1986 | Glenn ............................. 73/642 |
| 4,881,409 A | | 11/1989 | Roarty |
| 4,901,578 A | * | 2/1990 | Brill, III .......................... 73/623 |
| 6,272,437 B1 | * | 8/2001 | Woods et al. ................... 702/35 |
| 6,298,727 B1 | | 10/2001 | Fleming et al. |
| 6,980,688 B2 | * | 12/2005 | Wilk ............................. 382/152 |
| 2006/0181177 A1 | | 8/2006 | Osawa |
| 2008/0139946 A1 | | 6/2008 | Adachi et al. |
| 2009/0133501 A1 | | 5/2009 | Georgeson |
| 2009/0301203 A1 | | 12/2009 | Brussieux |

FOREIGN PATENT DOCUMENTS

| DE | 199 52 407 A1 | 5/2001 |
| DE | 20 2004 008 489 U1 | 9/2004 |
| EP | 1 761 104 A1 | 3/2007 |
| FR | 958 531 | 3/1950 |
| WO | 2008/010711 A1 | 1/2008 |

OTHER PUBLICATIONS

International Search Report of PCT/EP2011/065212.

* cited by examiner

*Primary Examiner* — J M Saint Surin
(74) *Attorney, Agent, or Firm* — Laurence A. Greenberg; Werner H. Stemer; Ralph E. Locher

(57) ABSTRACT

An apparatus internally inspects a workpiece having a hollow cylindrical hole. The apparatus contains an ultrasound transducer configuration having a plurality of ultrasound transducer elements, which are arranged in at least one row, one next to the other, in an elastically deformable carrier which has the form of a segment of a hollow cylinder and has a plurality of sliding pimples which extend in the longitudinal direction of the carrier and project with a protrusion in the radial direction beyond the transmitting and/or receiving surfaces of the ultrasound transducer elements.

10 Claims, 2 Drawing Sheets

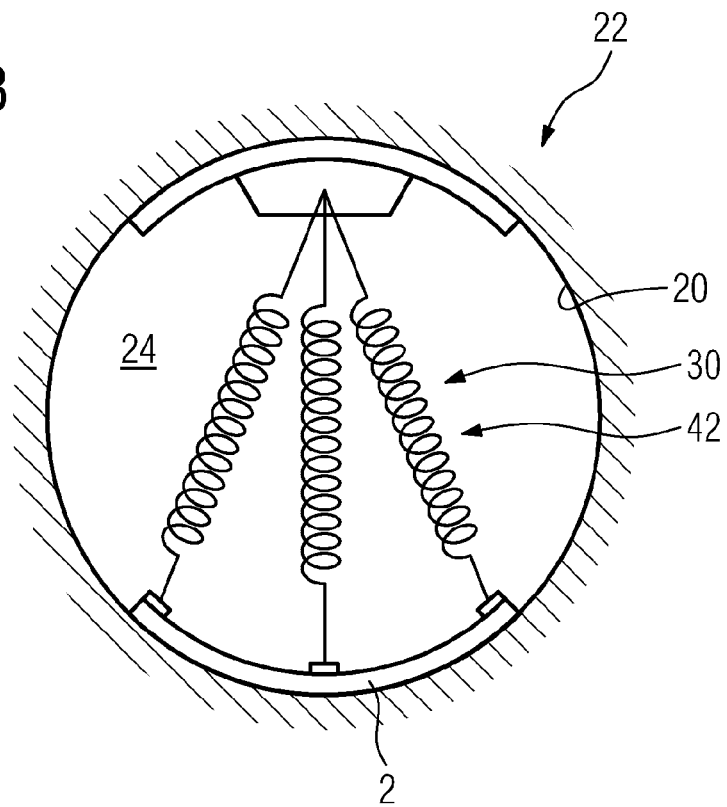
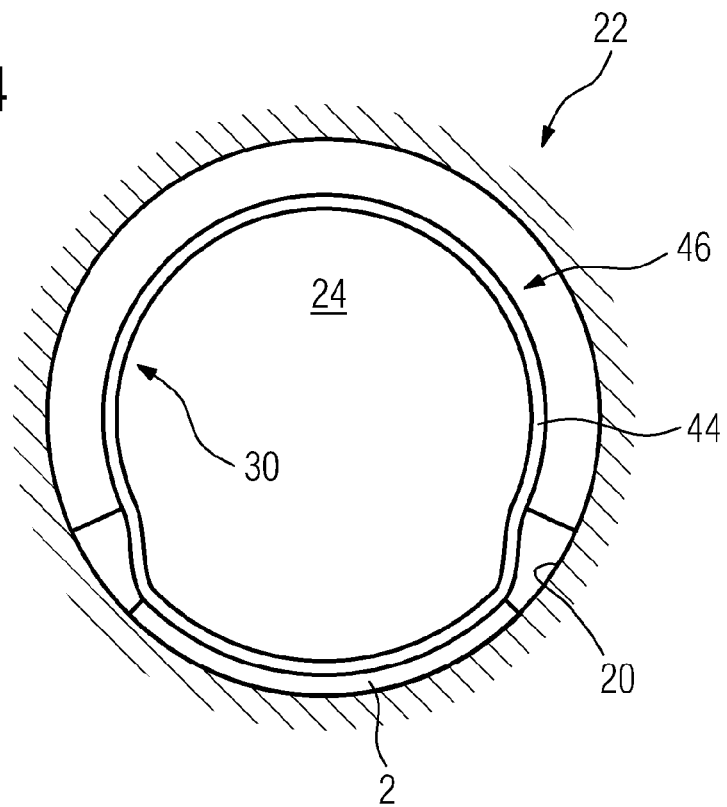

APPARATUS FOR INTERNAL INSPECTION OF A WORKPIECE HAVING A HOLLOW CYLINDRICAL HOLE

CROSS-REFERENCE TO RELATED APPLICATION

This application is a continuation, under 35 U.S.C. §120, of copending international application No. PCT/EP2011/065212, filed Sep. 2, 2011, which designated the United States; this application also claims the priority, under 35 U.S.C. §119, of German patent application No. DE 10 2010 040 274.5, filed Sep. 6, 2010; the prior applications are herewith incorporated by reference in their entireties.

BACKGROUND OF THE INVENTION

Field of the Invention

The invention relates to an apparatus for internal inspection of a workpiece having a hollow cylindrical hole.

Workpieces with an introduced hollow cylindrical hole, for example hollow screws or shafts, are frequently inspected with the aid of ultrasound starting from the hole side. Such an inspection technique is also designated as a boresonic inspection. As a rule, for this purpose an ultrasound transducer is inserted into the hole and guided there along a helical path. The ultrasound transducers used are in this case either conventional individual transducers or ultrasound transducer arrays that are constructed from a multiplicity of individual transducer elements and are operated using the emitter array inspection technique. In particular, because of the multiplicity of measuring channels, the phased array inspection technique with an ultrasound transducer array that is guided in a helical movement on the inner circumference of the hollow cylindrical hole requires a complicated slip ring transmission of the signals to and from the individual transducer elements of the ultrasound transducer array.

SUMMARY OF THE INVENTION

It is accordingly an object of the invention to provide an apparatus for the internal inspection of a workpiece having a hollow cylindrical hole which overcomes the above-mentioned disadvantages of the prior art devices of this general type, which enables the workpiece to be inspected reliably starting from an internal surface of the hole with little technical outlay.

With the foregoing and other objects in view there is provided, in accordance with the invention an apparatus for internally inspecting a workpiece having a hollow cylindrical hole. The apparatus contains an elastically deformable carrier having a form of a segment of a hollow cylinder and a front side, and an ultrasound transducer configuration having a plurality of ultrasound transducer elements disposed in at least one row next to one another in the elastically deformable carrier. The ultrasound transducer elements have transmitting and receiving surfaces. A plurality of sliding knobs extend in a longitudinal direction of the elastically deformable carrier and project with a protrusion in a radial direction along the transmitting and receiving surfaces of the ultrasound transducer elements. The elastically deformable carrier has a number of cutouts corresponding to a number of the ultrasound transducer elements. A matching film is disposed on the front side and functions as a matching layer for covering the cutouts. The ultrasound transducer elements are inserted in the cutouts and bonded to the matching film via the transmitting and receiving surfaces.

In accordance with these features, the apparatus includes an ultrasound transducer arrangement with a plurality of ultrasound transducer elements that are arranged in at least one row next to one another in an elastically deformable carrier that has the form of a segment of a hollow cylinder and has a plurality of sliding knobs that extend in its longitudinal direction and project with a protrusion in a radial direction along the transmitting and receiving surfaces of the ultrasound transducer elements.

The invention takes account here, on the one hand, of the fact that, particularly in small holes, it is impossible to couple the ultrasound transducer elements using the immersion or pilot technique with a long pilot path, since there is not sufficient space for this purpose, and the run time of the ultrasound in the pilot path must be longer than its run time inside the inspection item, since otherwise the multiple echoes produced within the pilot path would be superimposed on the actual useful signal from the inspection item. However, on the other hand, problems occur in relation to coupling in direct contact with the surface of the workpiece to be examined in the case of extended ultrasound transducer arrangements, because large changes in the measurement signals received by the transducer elements can then occur owing to small coupling gaps, which unavoidably vary from transducer element to transducer element. The use of sliding knobs that project with a defined protrusion beyond the transmitting or receiving surfaces of the ultrasound transducer array gives rise to a defined narrow coupling gap in the case of which—in conjunction with an optimized matching film for matching the oscillator impedance to the impedance of the coupling medium—on the one hand, the so-called ringing of the received measurement signals that is caused by the coupling gap can largely be avoided, and in which, on the other hand, a uniform coupling is also ensured for the individual transducer elements of an ultrasound transducer array.

Owing to the coupling of the ultrasound signals into and/or out of the workpiece via a small coupling gap that is preferably between $0.4\lambda$ and $1.1\lambda$, and to the thereby reduced overall height of the ultrasound transducer arrangement, and owing to the use of an elastically deformable carrier that has the form of a segment of a hollow cylinder, a multiplicity of ultrasound transducer elements can be arranged next to one another on the carrier in a circumferential direction such that a larger region of the inside circumference of the hole can be covered in one axial inspection run. Owing to their comparatively small dimension, which is preferably of the order of magnitude of $\lambda/2$ of the longitudinal wavelength, the individual ultrasound transducer elements themselves generate a sound beam with very large aperture angles. By superimposing the signal information of the individual ultrasound transducer elements and, in particular, by using the dynamic signal profiles resulting from axial movement of the probe ("synthetic aperture"), it is possible to reconstruct the detected indications, this being equivalent to the inspection statement of "conventional" phased array inspection technique. It is thereby possible to carry out a complete internal inspection with the aid of a few axial inspection runs such that there is no longer any need for a movement of the carrier including the ultrasound transducer arrangement in a circumferential direction, or for correspondingly complicated slip-ring contacts for signal transmission. This additionally reduces the overall size of the ultrasound transducer arrangement.

When the carrier has the form of a segment of a hollow circular cylinder that occupies at least a quarter of the circumference of the circular cylinder, it is possible to inspect the entire hole with at most four axial runs.

In a further advantageous refinement of the invention, the ultrasound transducer elements are arranged in the carrier in a plurality of mutually parallel rows such that they form a two-dimensional matrix. The inspection statement is substantially improved thereby.

The production of the apparatus is simplified when the carrier is provided with a number of cutouts corresponding to the number of the ultrasound transducer elements and, on its front side, with a matching film that serves as matching layer and covers the cutouts, and the ultrasound transducer elements are inserted into the cutouts and bonded to the matching film with their transmitting and/or receiving surfaces.

In a further preferred embodiment, there is arranged in the carrier at least one channel for guiding a coupling fluid which communicates with openings arranged in the front side of the carrier. The coupling fluid flows out of the openings into the gap formed by the skids between the inner surface and the ultrasound transducer elements and, furthermore, improves the acoustic coupling of the ultrasound transducer array to the inner surface of the workpiece. Moreover, the coupling fluid, in particular an oil, reduces the wear of the skids which, in particular, consist of a ceramic material, and so the defined coupling gap set up is maintained over a long period of use.

In a further particularly preferred refinement of the invention, there is provided a pressure exerting device that acts on the rear side of the carrier and can be supported on the inner wall of the hole averted from the carrier. This ensures a uniform coupling gap even in the case of varying geometric dimensions of the hole—deviation from an ideal circular cylindrical form.

Other features which are considered as characteristic for the invention are set forth in the appended claims.

Although the invention is illustrated and described herein as embodied in an apparatus for internal inspection of a workpiece having a hollow cylindrical hole, it is nevertheless not intended to be limited to the details shown, since various modifications and structural changes may be made therein without departing from the spirit of the invention and within the scope and range of equivalents of the claims.

The construction and method of operation of the invention, however, together with additional objects and advantages thereof will be best understood from the following description of specific embodiments when read in connection with the accompanying drawings.

BRIEF DESCRIPTION OF THE SEVERAL VIEWS OF THE DRAWING

FIG. 3 is an illustration showing the apparatus in a fashion operationally connected to a pressure exerting device; and FIG. 4 is an illustration showing an alternative refinement of a pressure exerting device acting on the apparatus.

DETAILED DESCRIPTION OF THE INVENTION

Figure 1:
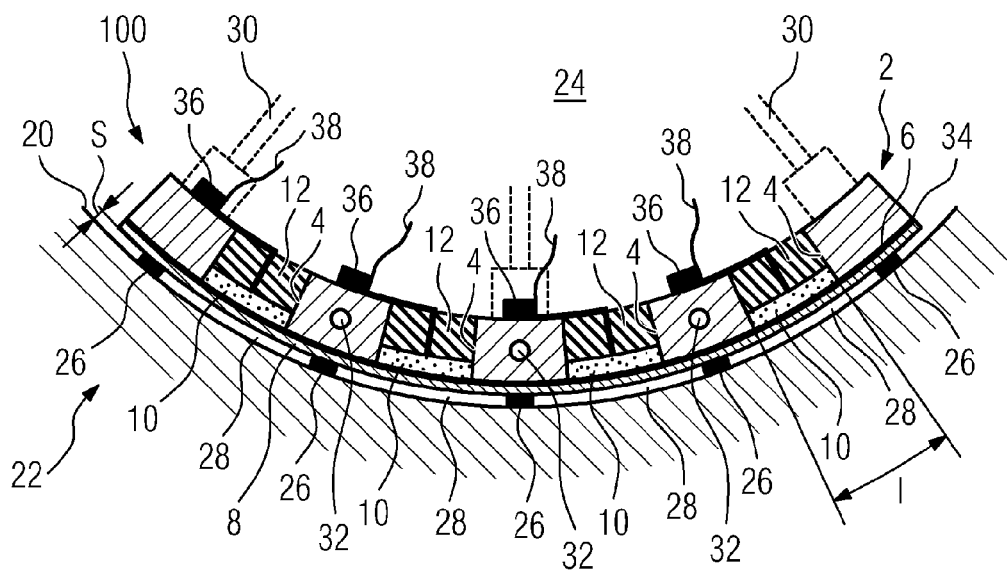
FIG. 1 is a diagrammatic, cross-sectional view of an apparatus in an operating position on an inner surface of a hole located in a workpiece according to the invention.

Referring now to the figures of the drawing in detail and first, particularly, to FIG. 1 thereof, there is shown an apparatus that contains a carrier 2 that is provided with a plurality of cuboid cutouts 4 which are covered on a convex front side of the carrier 2 by a matching film 8 with the aid of which the cutouts 4 are sealed on a front side 6 of the carrier 2. Ultrasound transducer elements 10 are respectively introduced into the cutouts 4 and bonded to the matching film 8. A thickness of the matching film 8 is approximately a quarter of a wavelength $\lambda$ of the ultrasound used for inspection, and serves the purpose of matching the acoustic impedance of the transducer elements 10 to the acoustic impedance of a coupling fluid. The matching film 8 is, moreover, optimized with regard to its sound damping properties, which contributes additionally to minimizing the so-called ringing of the ultrasound signals.

The ultrasound transducer elements 10 have a rectangular transmitting and/or receiving surface with a length l in a circumferential direction of typically $2\lambda$ to $3\lambda$, and a width b (FIG. 2) in the longitudinal direction of typically $\lambda/2$. Damping bodies 12 are integrally cast into the cutouts 4 in each case adjoining the rear side of the ultrasound transducer elements 10.

The carrier 2 and the damping body 12 are elastically deformable, in the absence of forming forces the carrier 2 having the form of a segment of a hollow cylinder and a basic shape matched to the radius of the hole 24 located in a workpiece 22. The carrier 2 extends in a longitudinal direction perpendicular to the plane of projection. The ultrasound transducer elements 10 are arranged with their narrow sides next to one another in at least one row 100 extending in a circumferential direction of the carrier 2 and running parallel to the plane of projection, only one row 100 containing four ultrasound transducer elements 10 being represented, for reasons of clarity. In a practical exemplary embodiment, an ultrasound transducer arrangement formed by the ultrasound transducer elements 10 contains, for example, 6 rows 100 each having 8 ultrasound transducer elements 10.

Bonded onto the matching film 8 between the ultrasound transducer elements 10 are a plurality of flat sliding knobs 26 between which the ultrasound transducer elements 10 are respectively arranged, and with which a defined coupling gap 28 is produced between an inner surface 20 of the hole 24 and the matching film 8, that is to say the transmitting and/or receiving surfaces of the ultrasound transducer elements 10, when the carrier 2 is pressed against the inner surface 20 with the aid of a pressure exerting device 30 (only indicated in a partial illustration by dashes) such that the sliding knobs 26 bear against the inner surface 20 without a gap. The protrusion s of the sliding knobs 26 beyond the matching film 8, that is to say beyond the transmitting and/or receiving surfaces of the ultrasound transducer array 10, and the width, resulting in this way, of a coupling gap 28 are in this case preferably between $0.4\lambda$ and $1.1\lambda$.

Arranged parallel to the longitudinal direction, that is to say perpendicular to the plane of projection, in the carrier are longitudinal channels 32 through which a coupling fluid can be introduced via the exit openings 40 (FIG. 2) into the coupling gap 28 formed between the matching film 8 and the inner surface 20 of the hole 24.

Electrical contact is made with the ultrasound transducer elements 10 on the transmitting and/or receiving surfaces via a thin conductive layer 34 with a thickness of only a few μm that is applied to the flat side, facing the ultrasound transducer elements 10, of the matching film 8, conductive foil strips making contact with the layer 34, and via contact clips 36 that are arranged on the rear side of the carrier 2, for example bonded, and which, via contact tongues—cast into the damping bodies 12—produce a conductive connection to the soldered on contact wire 38 between the rear side of each individual ultrasound transducer element 10.

Figure 2:
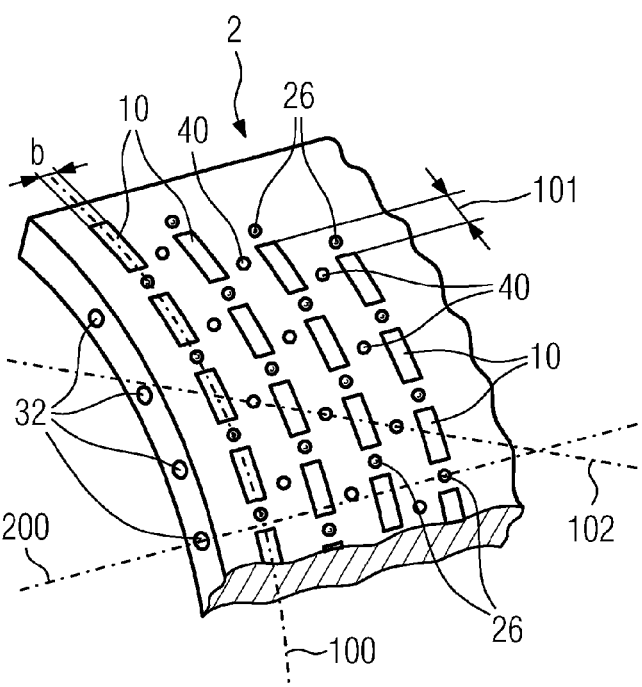
FIG. 2 is a diagrammatic, perspective view of the apparatus.

In accordance with FIG. 2, the ultrasound transducer elements 10 are arranged in a plurality of rows 100 in the carrier 2 which are arranged sequentially in the longitudinal direction of the carrier 2 and arranged parallel to one another. The ultrasound transducer elements 10 of adjacent rows 100 are arranged offset from one another in the circumferential direction with an offset 101 so as to produce a matrix-shaped ultrasound transducer arrangement whose gaps 102 are oriented obliquely to the longitudinal axis 200 of the carrier 2, and obliquely to its circumferential direction. Such an offset 101 ensures that in the case of an axial inspection run in the hole the workpiece is completely recorded on its partial circumference covered by the carrier 2 and is displayed with a good circumferential resolution.

In the perspective illustration of FIG. 2, there are to be seen, moreover, openings 40 that are arranged in the front side of the carrier 2 or the matching film 8 and which open into the coupling gap 28 (FIG. 1) fixed by the sliding knobs 26 and communicate with the longitudinal channels 32.

Illustrated in FIG. 3 in a schematic sketch is the carrier 2 with a pressure exerting device 30, which is acting on it and is resiliently supported on the inner surface 20 of the hole 24 opposite the carrier 2, and presses the carrier 2 resiliently against the inner surface 20, for example via a spring arrangement 42, symbolically illustrated by helical springs, such that the elastically deformable carrier 2 bears against the inner surface 20 with an identical coupling gap with its sliding knobs (not illustrated in FIG. 3 for reasons of clarity), even if the inner surface deviates from the ideal circular basic shape.

An alternative refinement of the pressure exerting device 30 is illustrated in FIG. 4 in accordance with which an inflatable tube 44 is inserted into the hole 24 and likewise presses the carrier 2 against the inner surface 20 of the hole 24 and is supported at the rear on the inner surface 20 via an opposing shell 46.

The invention claimed is:

1. An apparatus for internally inspecting a workpiece having a hollow cylindrical hole, the apparatus comprising:
    an elastically deformable carrier having a form of a segment of a hollow cylinder and a front side;
    an ultrasound transducer configuration having a plurality of ultrasound transducer elements disposed in at least one row next to one another in said elastically deformable carrier, said ultrasound transducer elements having transmitting and receiving surfaces;
    a plurality of sliding knobs extending in a longitudinal direction of said elastically deformable carrier and projecting with a protrusion in a radial direction along said transmitting and receiving surfaces of said ultrasound transducer elements;
    said elastically deformable carrier having a number of cutouts formed therein corresponding to a number of said ultrasound transducer elements; and
    a matching film disposed on said front side and functioning as a matching layer for covering said cutouts, said ultrasound transducer elements inserted in said cutouts and bonded to said matching film via said transmitting and receiving surfaces.

2. The apparatus according to claim 1, wherein said sliding knobs are formed from a ceramic material.

3. The apparatus according to claim 1, wherein said protrusion being 0.4 to 1.1 times a wavelength $\lambda$ of ultrasound used for the inspecting.

4. The apparatus according to claim 1, wherein said ultrasound transducer elements are disposed in said elastically deformable carrier in a plurality of rows disposed sequentially in the longitudinal direction and in a manner parallel to one another.

5. The apparatus according to claim 1, wherein said matching film has an electrically conductive layer on a flat side facing said elastically deformable carrier.

6. The apparatus according to claim 1, further comprising an elastically deformable damping body disposed on a rear side of said ultrasound transducer elements.

7. The apparatus according to claim 6, further comprising:
    a contact clip;
    a contact wire; and
    a contact tongue serving as a signal connection to said ultrasound transducer elements and integrally cast into said elastically deformable damping bodies and is part of said contact clip that is disposed on a rear side of said elastically deformable carrier and to which said contact wire is respectively soldered.

8. The apparatus according to claim 1, wherein said elastically deformable carrier has openings formed therein and at least one channel formed therein for guiding a coupling fluid which communicates with said openings disposed in a front side of said elastically deformable carrier.

9. The apparatus according to claim 1, wherein said elastically deformable carrier has a form of said segment of the hollow circular cylinder that occupies at least a quarter of a circumference of a circular cylinder.

10. The apparatus according to claim 1, further comprising a pressure exerting device for acting on a rear side of said elastically deformable carrier and is being supported on an inner wall of the hole averted from said elastically deformable carrier.

* * * * *